(12) United States Patent
Nilsson et al.

(10) Patent No.: US 8,208,997 B2
(45) Date of Patent: Jun. 26, 2012

(54) NON-INVASIVE METHOD TO MONITOR MICROCIRCULATION

(75) Inventors: Gert Nilsson, Linköping (SE); Folke Sjöberg, Linköping (SE)

(73) Assignee: Wheelsbridge AB, Linkoping (SE)

( * ) Notice: Subject to any disclaimer, the term of this patent is extended or adjusted under 35 U.S.C. 154(b) by 1102 days.

(21) Appl. No.: 10/592,024

(22) PCT Filed: Apr. 18, 2005

(86) PCT No.: PCT/SE2005/000554
§ 371 (c)(1),
(2), (4) Date: Sep. 7, 2006

(87) PCT Pub. No.: WO2005/099572
PCT Pub. Date: Oct. 27, 2005

(65) Prior Publication Data
US 2007/0146686 A1    Jun. 28, 2007

(30) Foreign Application Priority Data
Apr. 19, 2004 (SE) ...................................... 0401004

(51) Int. Cl.
*A61B 5/02* (2006.01)
(52) U.S. Cl. ......... 600/479; 600/476; 600/478; 382/128
(58) Field of Classification Search ................. 600/450, 600/453–454, 465, 468, 473, 476, 478–481, 600/483–485; 382/274
See application file for complete search history.

(56) References Cited

U.S. PATENT DOCUMENTS
4,366,529 A * 12/1982 Takahashi et al. ............. 362/4
(Continued)

FOREIGN PATENT DOCUMENTS
JP        05-007559 A1    1/1993
(Continued)

OTHER PUBLICATIONS

Spie's OEMagazine, Nov. 2003, Christopher Cook, Rheologics Inc., "Lighting Up VEINIMAGING".
(Continued)

*Primary Examiner* — Tse Chen
*Assistant Examiner* — Joel F Brutus
(74) *Attorney, Agent, or Firm* — Porter Wright Morris & Arthur (57) ABSTRACT

This invention relates to the non-invasive determination of the degree of vasoactivity in the microcirculation in a tissue caused by a drug, disease, injury normal or pathological regulation. More specifically, the invention relates to a method of determining the influence on microcirculation in living tissue from an irritative agent, drugs, disease, injuries normal or pathological regulation including, illuminating a tissue surface with polarized light, collecting the backscattered light through a polarizing filter, detecting the backscattered and polarized light by a photo-sensitive array, transferring the collected information in digital form to a computing device, separating the collected information into at least two data matrixes, each representing a specific wavelength range and generating an output data matrix by processing corresponding values in at least two data matrixes by an algorithm, wherein each value in said output data matrix represents the amount of influence on the microcirculation in a source point of the tissue. Thereby a representation of the tissue microcirculation is obtained.

25 Claims, 6 Drawing Sheets

U.S. PATENT DOCUMENTS

| | | | |
|---|---|---|---|
| 4,913,159 A * | 4/1990 | Gardin et al. | 600/456 |
| 5,361,769 A * | 11/1994 | Nilsson | 600/479 |
| 5,620,000 A | 4/1997 | Zinser et al. | |
| 5,699,797 A * | 12/1997 | Godik | 600/475 |
| 5,983,120 A * | 11/1999 | Groner et al. | 600/310 |
| 6,061,176 A * | 5/2000 | Shih | 359/368 |
| 6,122,042 A * | 9/2000 | Wunderman et al. | 356/73 |
| 2002/0091320 A1* | 7/2002 | Crutchfield et al. | 600/454 |
| 2004/0208393 A1* | 10/2004 | Nakakuki | 382/274 |

FOREIGN PATENT DOCUMENTS

| | | |
|---|---|---|
| JP | 07-146305 A1 | 6/1995 |
| JP | 11-197126 A1 | 7/1999 |
| JP | 2001-046348 A1 | 2/2001 |
| WO | 9822023 | 5/1998 |
| WO | 0075637 | 12/2000 |
| WO | 2004010118 | 1/2004 |
| WO | 2004010862 | 2/2004 |

OTHER PUBLICATIONS

Database WPI, Week 200216, Derwent Publications Ltd., London, GB; Class P31, AN 2002-116649 & JP 2001-46348 A (Omega Wave KK), Feb. 20, 2001.

Patent Abstracts of Japan, vol. 017, No. 270, May 26, 1993, and JP 5-007559 A (Advance Co Ltd), Jan. 19, 1993.

Office Action and English Translation from corresponding JP 2005-116940 dated Nov. 2, 2010.

* cited by examiner

NON-INVASIVE METHOD TO MONITOR MICROCIRCULATION

RELATED APPLICATIONS

This application is a 371 of PCT/SE2005/000554 filed Apr. 18, 2005 and claims priority under 35 U.S.C. §119 of Swedish Application No. 0401004-7 filed Apr. 19, 2004.

FIELD OF INVENTION

This invention relates to the non-invasive determination of the degree of vasoactivity in the microcirculation in a tissue caused by an irritative agent, drug, disease, injury, normal or pathological regulation.

BACKGROUND OF THE INVENTION

In medical practice, in the development of new drugs and in skin testing procedures it is important to determine physiological responses such as the degree of vasodilatation or vasoconstriction in the microcirculation following application of a vasoactive drug directly in contact with the skin or administrated by other routes. A suitable way of transdermal drug administration is by means of iontophoresis in order to support penetration of charged drug molecules through the epidermal layer or by topical application of the drug or agent.

Although the reddening of the skin generally can be seen by the naked eye, a more objective method is generally used in the medical setup. Laser Doppler perfusion imaging (Wårdell K., Jakobsson, A. J. and Nilsson, G. E. *Laser Doppler Perfusion Imaging by Dynamic Light Scattering. IEEE Trans BME*, Vol 40, No. 4, 309-316, 1993.) is a method that by sequentially scanning the tissue surface of interest, gives a quantitative measure of the increase in blood perfusion and thus a measure of the effect on the microvasculature of the vasoactive drug under study. Alternatively a single point laser Doppler perfusion monitor may be used for monitoring the tissue blood perfusion. Using the combined setup of iontophoresis and laser Doppler perfusion imaging, several critical parameters of iontophoresis—including current strength, effect of inflammatory processes, and vasoactive drug dosage (Droog E. J. and Sjöberg F. *Nonspecific vasodilatation during transepidermal iontophoresis—the effect of voltage over the skin, Microvascular Research,* 65(2003) 172-178; Droog, E. G., Henricsson, J., Nilsson, G. E. and Sjöberg, F. *A protocol for iontophoresis of acetylcholine and sodium nitroprusside that minimizes non-specific vasodilatory effects, Microvascular Research,* 67 (2004) 197-220)—have been studied and optimized. In clinical settings this combined technology of iontophoresis and laser Doppler perfusion imaging has been used in studies of the response to transepidermally applied vasoactive drugs in patients with diabetes (Morris, S. J., Shore, A. C. and Tooke, J. E. *Responses of the skin microcirculation to acetylcholine and sodium nitroprusside in patients NIDDM, Diabetologica* 38, 1337-1344, 1995) and in patients with Alzheimer's disease (Algotsson, A., Nordberg, A, Almkvist, O. and Winblad, B. *Skin vessel reactivity is impaired in Alzheimer's disease. Neurobiol Aging.* 1995 July-August; 16(4):577-82).

Laser Doppler perfusion imaging (and monitoring) is, however, a technology not very well suited for applications in primary care or in the office of the general practitioner, because of high cost and to some extent cumbersome handling and image interpretation. Besides, laser Doppler perfusion imaging (and monitoring) gives a representation of the tissue blood perfusion rather than the vasodilatation or vasoconstriction of the microvascular bed as a response to the vasoactive agent.

A companion technology entitled Orthogonal Polarization Spectroscopy using a selected illumination band of wavelengths has earlier been used in microscopes in an attempt to visualize the detailed architecture of the smallest vessels of the microcirculation (Uhl, E., Lehmberg, J., Steiger, H. J. and Messmer, K *Intraoperative detection of early microvasospasm in patients with subarachnoid hemorrhage by using orthogonal polarization spectral imaging, Neurosurgery,* June 2003 52(6) 1307-15). The high degree of magnification required, however, makes this technology difficult to use in primary care and in the general practitioner's office, because of the inevitable relative movement between the microscope and the object. Besides, the end result is in best case a structural image of the minute vessels in a small area and gives no direct information about the average vasodilatation of a more extensive skin site.

Obviously, there is demand for a complementary technology, that can be applied in for example test laboratories for skin care product evaluation and in diabetes clinics and primary care at low costs to identify patients, who are at risk of acquiring more profound complications from diseases known to cause impaired circulation, for a preventing regimen or therapy.

DESCRIPTION OF INVENTION

It is an object of the present invention to provide for a method employing polarized light to produce a representation of how the microcirculation of a patient or a test subject is influenced by irritating agents, drugs, disease or injuries.

It is another object of the present invention to provide for reliable, quick and cheap method to determine if a patient suffering from underlying disease known to produce impairments in microcirculation is susceptible to acquire such complications and thereby need a change of regiment or therapy.

These and other objects will be apparent from the following specification and its appended claims.

In its most general form a method according to the present invention involves illumination of a target tissue, typically in the body periphery surface with polarized light. Backscattered and polarized light is collected with a polarized filter and detected by means of a photosensitive array. Arrangements to generate polarized light and polarizing filters are well known and will not be further discussed herein. A photosensitive array may be a digital camera that is capable of converting the incoming light having passed through the polarization filter into digital values. Alternatively, conventional types of sensors producing analog signals are conceivable and may be connected to an analog/digital converter of conventional nature. The person skilled in this technology may readily envision several suitable arrangements. The so collected, digitalized information is transferred to a computing device, wherein it is separated into at least two matrixes, each representing a specific, pre-selected wavelength range. The computing device is further adapted to generate an output data matrix by processing corresponding values of the matrixes by an algorithm. Each value in said output data matrix represents the amount of influence on the microcirculation in a source of point of the tissue, thereby obtaining a representation of the tissue microcirculation.

According to one embodiment of the invention, the method involves local application of a vasoactive agent before illuminating the target tissue. When suitable to support the delivery to the tissue receptors, iontophoresis can be employed.

Vasoactive agents may for example be well-known vasodilatators, such as acetylcholine, sodium nitroprusside, or combinations thereof. Combining vasodilatating agents with different modes of action such as by the endothelium or smooth muscles would also be conceivable in certain applications, as well as the use of vasoconstricting agents. The output data matrix may in one aspect of this embodiment be presented as an image colored or shaded in accordance with a scale of vasodilatation or vasoconstriction.

The polarizing filter preferably has a polarization direction orthogonal to that of said illuminating light. However, also other arrangements would be conceivable to persons skilled in the art.

In another embodiment values for normalization of the values of said data matrixes can be produced by simultaneously illuminating a reference area.

Preferably, the wavelength ranges represent specific colors, more preferably the colors, red green and blue. According to one preferred embodiment of the invention, the algorithm for generating the output data matrix employs the difference of the values of the data matrixes representing red and green color divided by the corresponding values in the data matrix representing the sum of the of the values of the data matrixes representing red and green color. The computing device may further include an algorithm for generating compensation for tissue color using the values in the data matrixes.

In an alternative embodiment of this invention the polarization filter in front of the photosensitive array has a polarization direction parallel to that of said illuminating light. By this arrangement only photons that have been backscattered in the superficial tissue layer will reach the photosensitive array, making the device selectively sensitive to the capillary blood circulation in the most superficial tissue layer only.

By capturing the images in a rapid sequence—as a video clip—and then compiling a movie, the fine dynamics of the microcirculation such as pulsatility can be detected. Using this aspect images representing the arterial and the venous side of the microcirculation can be generated, thereby making it possible to differentiate e.g. an arterial leg ulcer from a venous leg ulcer.

In another embodiment of the invention, the photosensitive array can be incorporated in an electrode (Camerode—Camera in an Electrode) that constitutes a wearable transducer device that facilitates continuous and mobile investigation of the most peripheral skin microcirculation in e.g. patients recovering from a heart attack or as early chock or blood pressure drop detection.

In yet another embodiment, the light from the illuminating light illuminates the tissue through flexible optical fibers. Another fiber or a bundle of oriented fibers brings the backscattered light back to the photosensitive array. By positioning the polarization filters at the distal end of the fibers—or by using polarization preserving light guides with the polarization filters positioned at the proximal end of the fibers—, the desired depth sensitivity can be attained and the microcirculation in body cavities can be investigated, thereby making it possible to detect tumours with elevated microcirculation.

The present invention is also directed at system for determining how the microcirculation of a living tissue is influenced by drugs, disease or injuries. The system generally comprises a light source combined with and a filter for illuminating a tissue surface with polarized light. Further, a polarizing filter is used for collecting the backscattered light and a photosensitive array detects the backscattered and polarized light and converts the detected light to a collected information of digital values. A computing device receives the collected information and separates it into at least two data matrixes, each representing a specific color an algorithm is employed that generates an output data matrix that represents the microcirculation. The system can be further adapted to cooperate with a mobile communication terminal capable of transmitting the output data matrix over a telecommunication network, such as a mobile network or a public fixed network, the Internet. The system can be integrated with a mobile communication terminal as details of a mobile telephone, or form separate units combined with local communication links. Accordingly the output information from the system can be adapted for direct communication with clinical care centers or for immediate analysis by the patient or clinically qualified persons.

According to a specific aspect of the invention, above mentioned methods are used to determine if a patient suffers from abnormalities in microcirculation, such as impaired microcirculation resulting from diabetes or Alzheimer's disease patient thereby is subjected to local administration of a vasoactive composition, whereupon any of the aforementioned methods are conducted. The resulting output matrix data or its representation is compared with a reference obtained from a healthy individual, or from the same patient prior to the administration of the vasoactive composition. In yet other applications the invention can be used for e.g. early detection of blood pressure drop during dialysis, early warning for vascular chock during surgery or intensive care and in detection of vascularized tumours of the skin or other body tissues.

The following part of the description demonstrates a preferred way of conducting present invention by way of examples. The skilled person will realize the possibility to deviate from what is exemplified and still operate within the inventive scope as earlier outlined.

DETAILED AND EXEMPLIFYING PART OF THE DESCRIPTION

One way of administrating the drug—typically acetylcholine (ACh) or sodium nitroprusside (SNP),—is by diffusion through the epidermal layer of the skin. This is facilitated by using e.g. a ring-shape electrode (A, FIG. 1) applied to the skin (B, FIG. 1) by double adhesive tape (C, FIG. 1). The chamber formed by this ring contains the vasoactive agent solved in 0.9% sodium chloride or other vehicle (D, FIG. 1). In some cases it is advantageous to cover the ring-shape electrode containing the vasoactive agent by a glass slide (E, FIG. 1). When a voltage, typically 10V (F, FIG. 1) is applied between this electrode and a reference electrode (G, FIG. 1) attached to skin some distance away from the active ring-shape electrode, a small electric current, typically 0.4 mA, is evoked, forcing the charged molecules of the active substance to penetrate the epidermal layer and reach the receptor molecules of the minute blood vessels in the microvasculature where they cause these vessels to dilate (increase their diameter). After some minutes of voltage application—by use of pulses or continuously—the actual skin area within the ring-shape electrode can be seen to become more red as more blood cells fill up the affected microvascular network. This procedure of administrating a vasoactive drug transepidermally is known under the name iontophoresis in the scientific literature. A suitable such system is Perlont 382 from Perimed AB (Järfälla Sweden).

Figure 2:
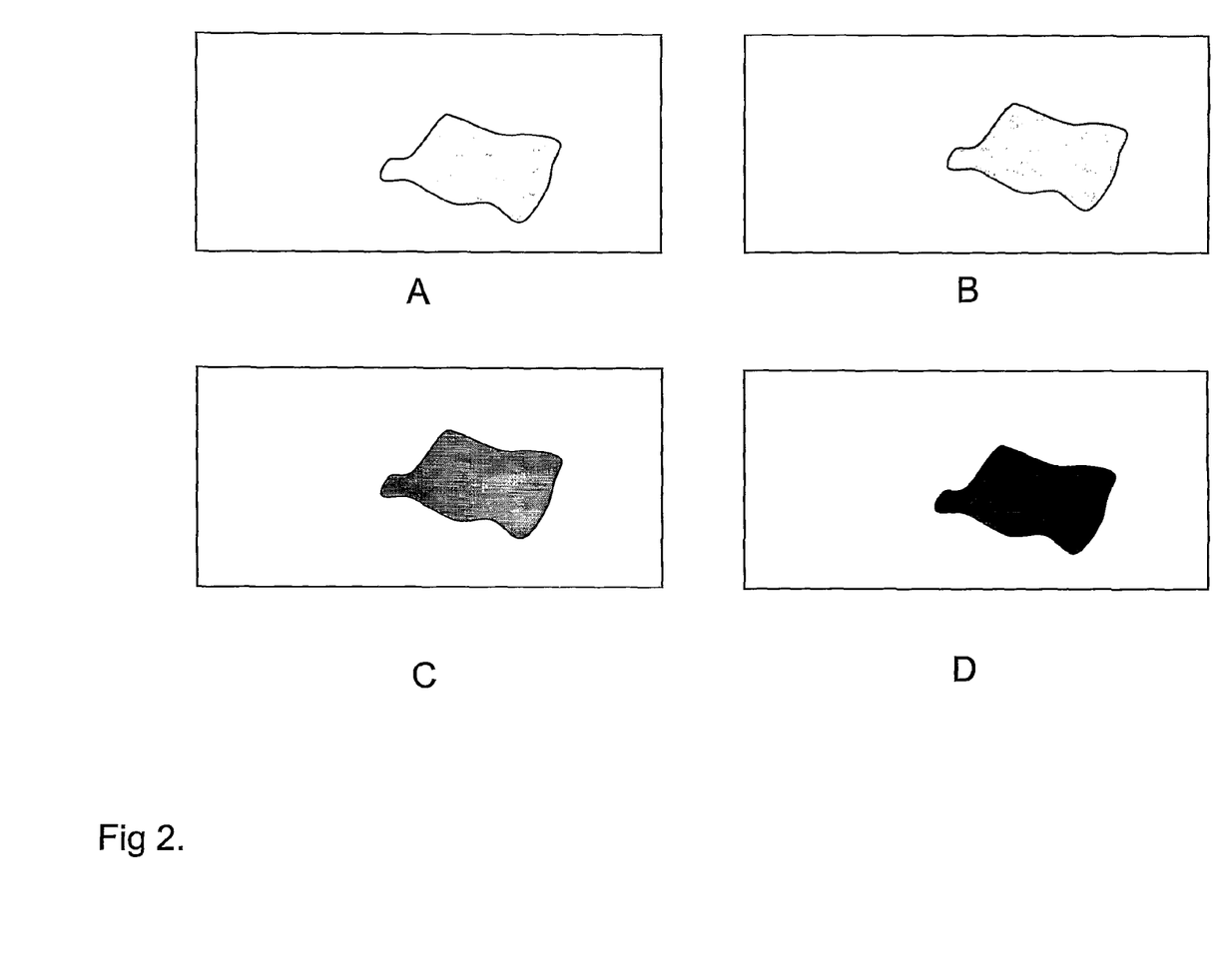
FIG. 2 demonstrates how methyl nicotinate amide successively produces successively increasing local vasodilatation in skin during a time period of 10 minutes (represented by the gray areas in the images)

Another way of administering the agent is by topical application on the skin. An example of applying methyl nicotinate amide on the skin, which produces local vasodilatation within minutes following the application, is demonstrated in FIG. 2 (A=0.5, B=2, C=5, D=10 minutes following application). This agent is frequently used in skin testing for assessing the sensitivity of the skin.

Figure 3:
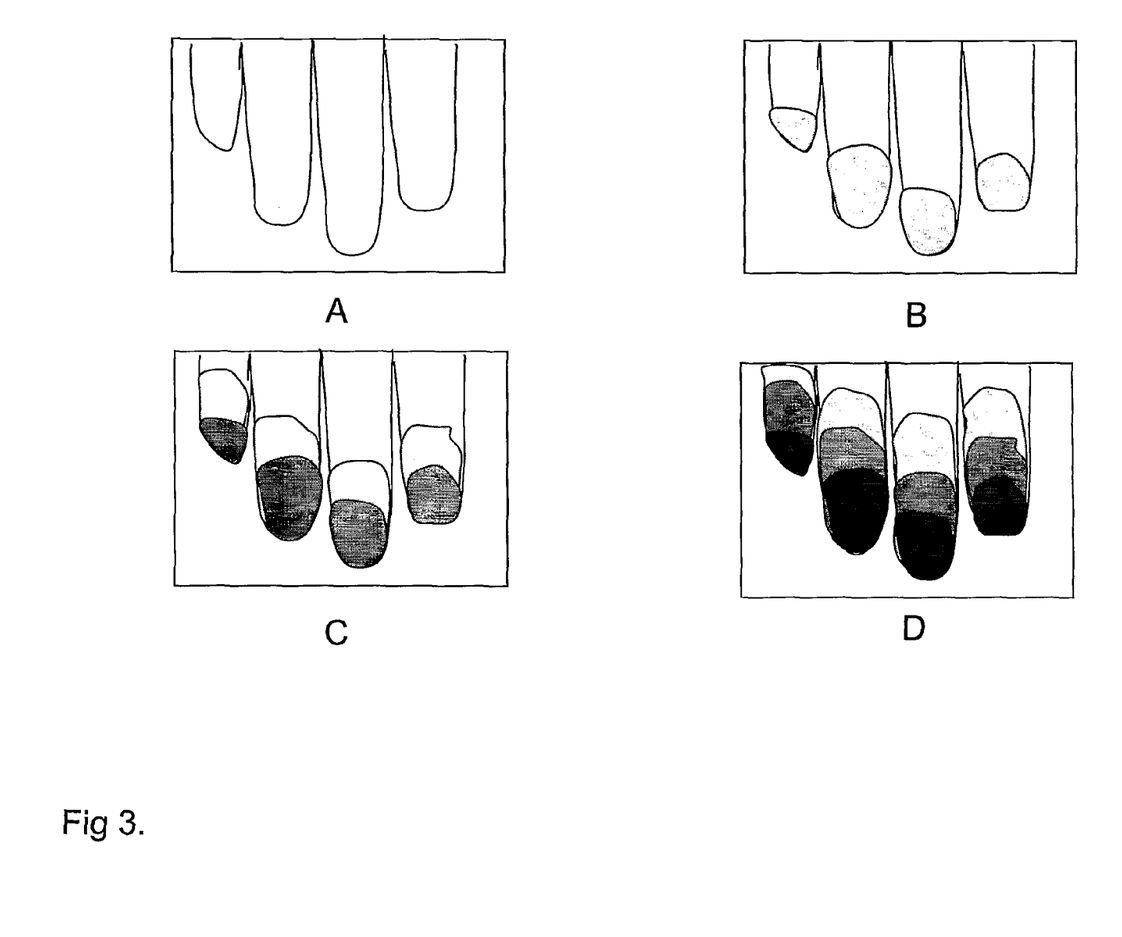
FIG. 3 shows how the microcirculation returns to the tips of the fingers in a hand following release of an occlusive cuff placed around the arm (represented by the gray areas in the image).

By collecting 15 images per second in the form of a video frame, rapid changes in the microcirculation can be visualized. In FIG. 3 the return of blood to the tips of the fingers during the reactive hyperemia phase following occlusion of the circulation is demonstrated (A=5, 10, 15, 20 seconds following the release of cuff pressure).

Figure 4:
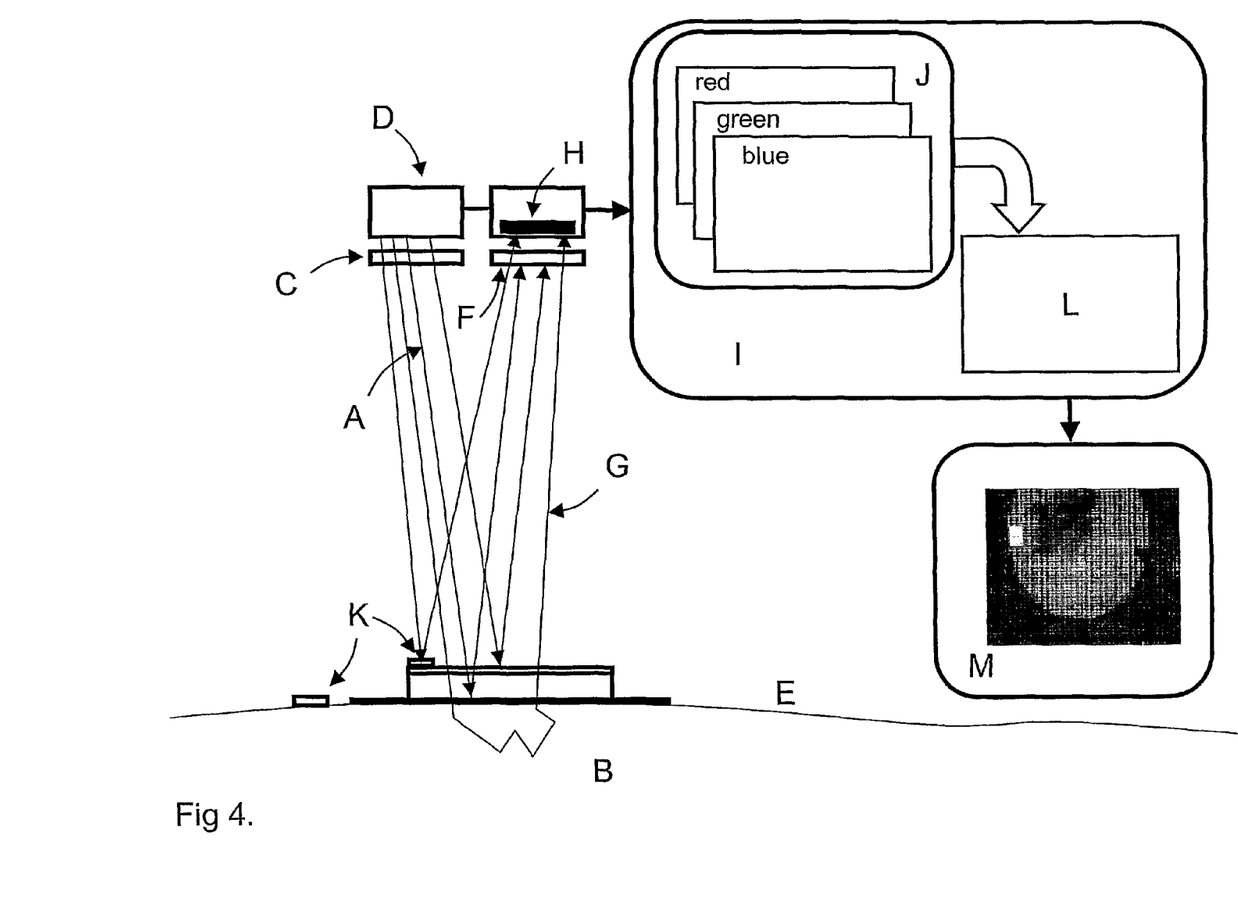
FIG. 4 shows light illuminating and data processing equipment according to the present invention.

In this example a modern digital camera technology is utilized, exemplified by Canon IXUS V3, Canon Svenska AB, Solna, Sweden. However, other photo-sensitive detector arrays are conceivable to document the vasodilatation of the skin or other tissue sites affected by the vasoactive drug. In this approach a flash of white light—or alternatively continuous light—(A, FIG. 4) illuminates the skin (B, FIG. 4) under study after having been linearly polarized by a polarizer (C, FIG. 4) positioned in front of the flash lamp—or a lamp delivering continuous light—(D, FIG. 4). In the skin surface (E, FIG. 4), a fraction of the polarized light is directly reflected towards the camera aperture with essentially no change in polarization. By placing a second polarizing filter (F, FIG. 4) in front of the camera aperture with the polarization direction orthogonal to that of the filter in front of the flash lamp, the photons directly reflected from the skin surface, the liquid surface and the slide are effectively stopped from reaching the camera. Photons that penetrate the skin surface suffer multiple scattering events at which they successively loose their linear polarization and become randomly polarized. Since a flash of white light—or continuous white light—is used, all colors of the visible spectrum are represented in the diffusely scattered light within the tissue. "Red" photons have a tendency to be less absorbed by the red blood cells than "green" and "blue" photons (see *Tuchin V V, Light-Tissue Interactions in Biomedical Photonics* (Ed. Vo-Dinh T., CRC Press 2003) Consequently the more red blood cells in the tissue (higher degree of vasodilatation), the higher is the absorption of "green" and "blue" photons in relation to the absorption of the "red" photons. Part of all diffusely scattered photons in the tissue is eventually reaching and escaping from the tissue surface. A fraction of those back-scattered and randomly polarized photons (G, FIG. 4) eventually penetrates the polarization filter in front of the camera and reaches the photosensitive array of detectors (H, FIG. 4).

The image captured by the digital camera or other photo-sensitive array of detectors in the present invention is transferred to a computer (I, FIG. 4) where color separation in red, green, and blue color (J, FIG. 4) is performed, each color represented by a data matrix with the size of the entire image matrix. In order to overcome the possible disadvantages of non-reproducible light energy in successive flashes—or fluctuations in continuous illumination—the backscattered light from a reference area (K, FIG. 4)—for which purpose the upper surface of the electrode ring or a specific marker area within the image field can be used—is utilized for normalization of the color data matrixes by dividing each color value in the original data matrixes by the average value for the same color representation in the reference area, thereby compensating for fluctuations in flash or continuous light intensity.

At least two of the normalized data matrixes representing the different colors are then further processed to form an output data matrix (L, FIG. 4), where each value corresponds to the amount of vasodilatation in the actual source point in tissue. In this example, the algorithm generates an output data matrix of which each element is calculated by subtracting the green value from the red value and divides the difference by the sum of the red and the green value of each element of the normalized original data matrixes. Depending on the situation, other algorithms based on the color data matrixes may be used to form and output data matrix representing the spatial variability of the vasodilatation in the tissue of interest and can also compensate for different degrees of pigmentation and oxygen saturation. This output data matrix can preferably be presented as a pseudo-color or shaded image on a computer display (M, FIG. 4). In practice, one image is generally captured before starting the iontophoresis procedure. This first image is used as a reference image. Images captured during the iontophoresis procedure and at the end of the procedure can then be referred to this first image in order to demonstrate the changes in vasodilatation instituted by the vasoactive agent that forms the active component of the iontophoresis procedure.

Although the above description of the invention discusses an electrode attached to the skin with double adhesive tape, several other alternatives are possible, such as sealing an electrode with a transparent slide and positioning it in a holder on which the tissue under study is placed during the measurement procedure.

EXAMPLE

Figure 5:
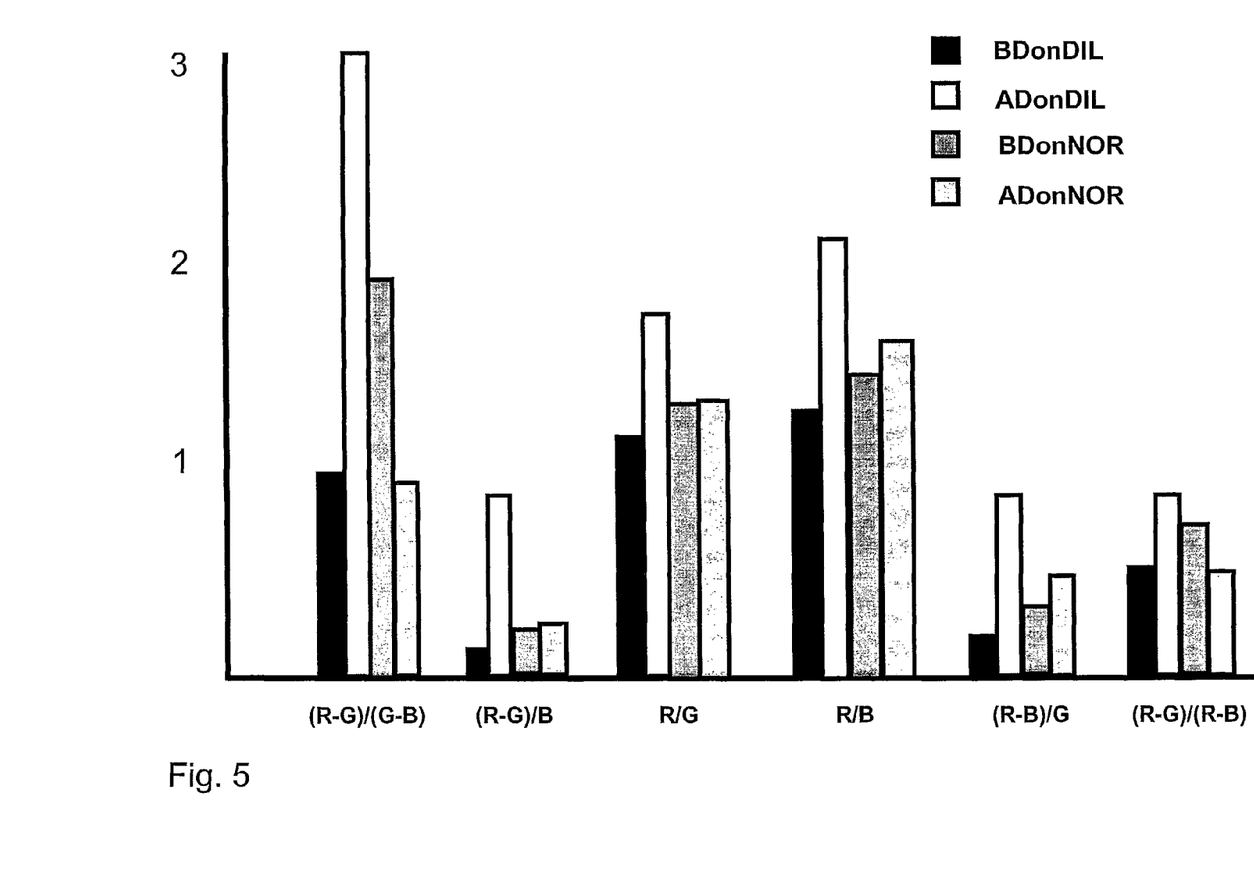
FIG. 5 shows an example how to present results from the output data matrix generated by the equipment of FIG. 4.

In a pilot study—following the production of vasodilatation in skin tissue—several different algorithms were applied in the generation of the output data matrix. The average value of the elements of this data output matrix is shown in FIG. 5 for the algorithms (R-G)/(G-B), (R-G)/B, RIG, RIB, (R-B)/G and (R-G)/(R-B), where R, G and B represent the average values of the data matrixes representing red, green and blue color. For each algorithm employed, the test was performed on the skin sites labelled (BDonDIL) representing a skin site Before Dilatation on DILated area, (ADonDIL) representing a skin site After Dilatation on DILated area, (BDonNOR) representing a skin reference site Before Dilatation on a NORmal not dilated area and ADonNORM representing a skin reference site After Dilatation on NORmal not dilated area respectively. As can be seen from the example in FIG. 5 the algorithm (R-G)/B gives the best discrimination among the algorithms tested. All color separations and algorithm calculations have been done in MatLab®.

Figure 6:
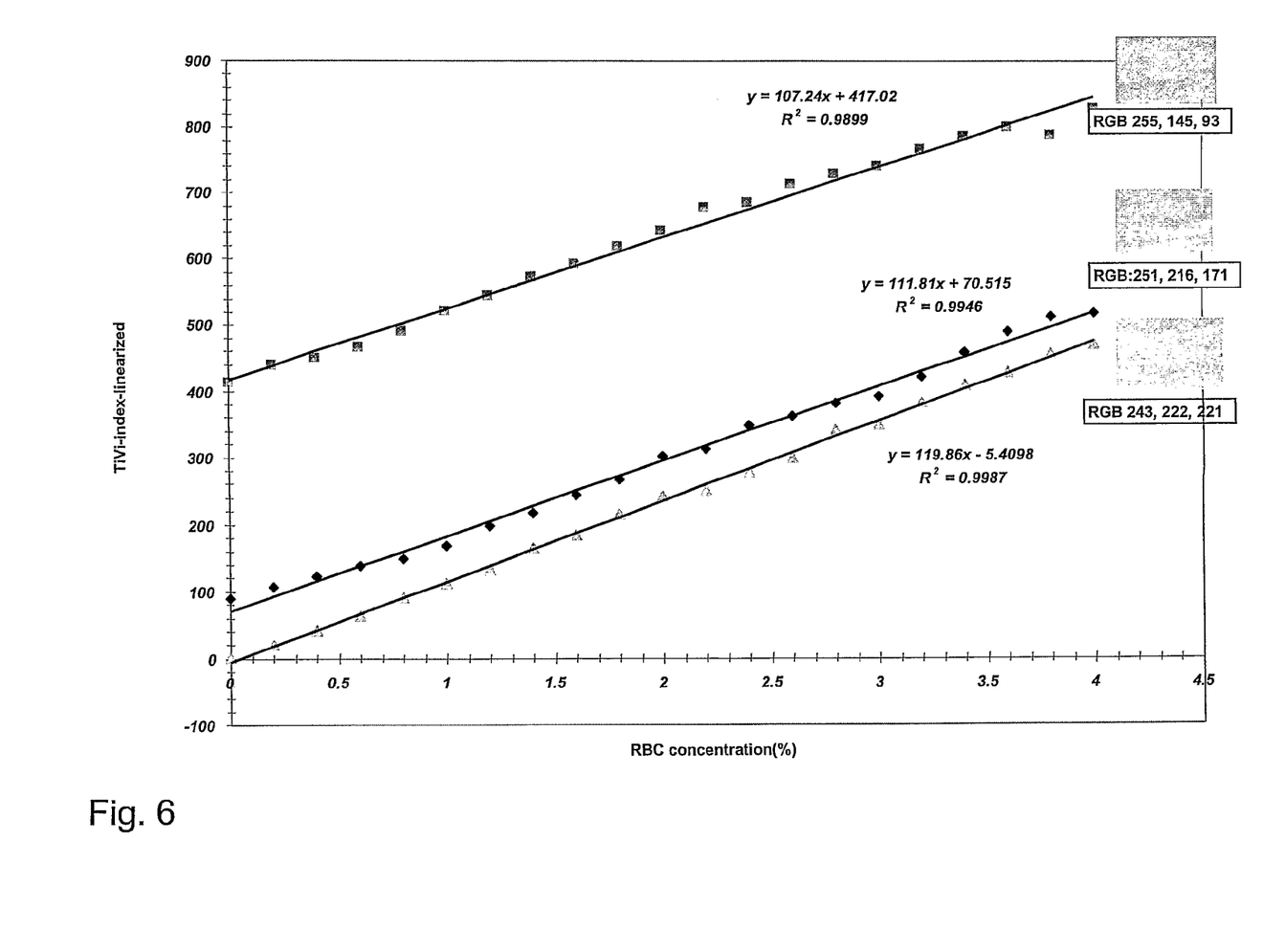
FIG. 6 shows calibration curves obtained by use of an in vitro model.

In another pilot study an in vitro model composed of transparent plastic tubings (Portex®, i.d. 0.8 mm) attached in a tightly back and forth manner to a background of skin simulated material and infused with varying concentrations of blood in saline suspension form 0-4%, was employed. Using an algorithm based on calculation of the difference of the "red" and "green" matrix, divided by the sum of the "red" and "green" matrix, the calibration curves displayed in FIG. 6 could be constructed for different background material color, the RGB (243, 222, 221) background best representing the color of blood less skin.

Figure 1:
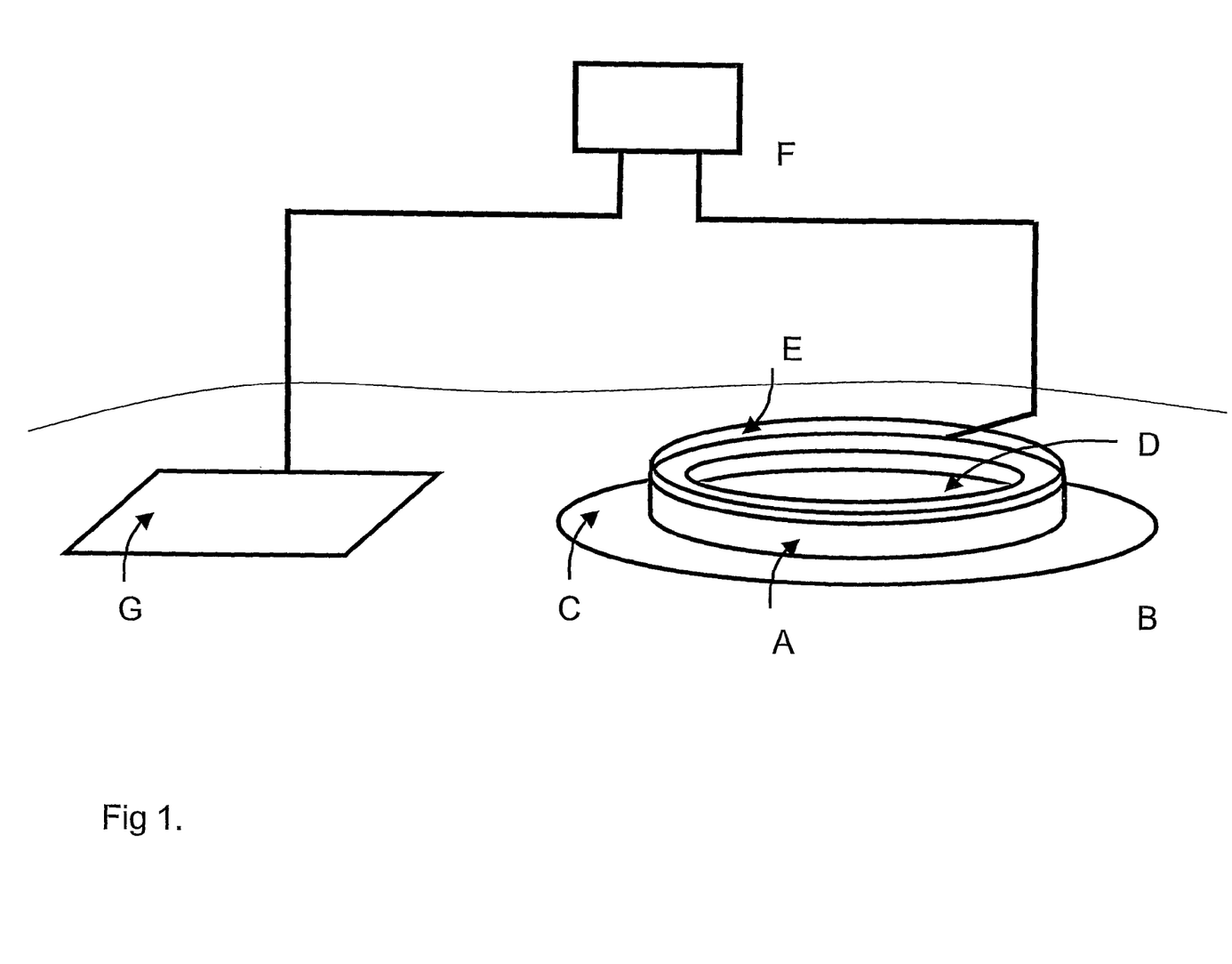
FIG. 1 shows an arrangement for iontophoresis suitable for the present invention.

Legend to FIG. 1.
A. Ring-shape electrode.
B. Skin.
C. Double-adhesive tape.
D. Vasoactive agent solved in 0.9% sodium chloride or other vehicle.
E. Glass slide.
F. Voltage source, supplying DC, AC or pulses.
G. Reference electrode.
Legend to FIG. 2.
Vasodilatation produced by methyl nicotineate amide topically applied to the skin. A=0.5, B=2, C=5, D=10 minutes following application. The darker the area, the higher the red blood cell concentration. In the real system the grayscale is replaced by a color scale.
Legend to FIG. 3.
Return of blood to the tips of the hand following the release of a pressure cuff positioned around the arm. A=5, 10, 15, 20 seconds following the release of cuff pressure. The darker the area, the higher the red blood cell concentration. In the real system the grayscale is replaced by a color scale.
Legend to FIG. 4.
A. Flash of white light or continuous white light.
B. Skin.
C. Polarizer.
D. Lamp delivering a flash of white light or continuous white light.
E. Skin surface.
F. Second polarizer.
G. Randomly polarized light.
H. Photo-sensitive array of detectors.
I. Computer.
J. Data matrixes representing red, green and blue color.
K. Reference area.
L. Output data matrix.
M. Computer display
Legend to FIG. 5.
Results using different algorithms
Legend to FIG. 6.
Calibration curves obtained by use of an in vitro model.

The invention claimed is:

1. A system for determining microcirculation of a living tissue comprising: (i) a white light source and a filter capable of illuminating a tissue surface with polarized light, (ii) a polarizing filter adapted to collect backscattered light subjected to multiple scattering events in the tissue; (iii) a photosensitive array capable of detecting the backscattered and polarized light and converting the detected light to a collected information of digital values; and (iv) a computing device adapted to receive said collected information, adapted to separate the collected information into data matrixes representing red, blue and green colors, respectively, and adapted to employ an algorithm to the data matrixes to generate an output data matrix representing the red blood cell concentration of the microcirculation.

2. A method of determining the influence on microcirculation in living tissue from drugs, disease, injuries or normal regulation, employing the system of claim 1, including: (i) illuminating a tissue surface with polarized light from the light source and filter; (ii) collecting backscattered light subjected to multiple scattering events in the tissue through the polarizing filter; (iii) detecting the backscattered and polarized light by the photosensitive array and converting the detected light to a collected information of digital values; (iv) transferring the collected information in digital form to the computing device; (v) separating the collected information into data matrixes representing red, blue and green colors, respectively; and (vi) generating an output data matrix by processing corresponding values in the data matrixes by an algorithm, wherein each value in said output data matrix represents the amount of influence on the microcirculation in a source point of the tissue, thereby obtaining a representation of the red blood cell concentration of the tissue microcirculation.

3. A method according to claim 2 including subjecting said tissue to local administration of a vasoactive agent.

4. A method according to claim 3, wherein iontophoresis is employed to support the administration of said vasoactive agent.

5. A method according to claim 3, wherein said vasoactive agent is a vasodilator selected from the group consisting of acetylcholine and sodium nitroprusside.

6. A system according to claim 1 comprising means for presenting said output data matrix as an image of vasodilatation or vasoconstriction, colored or shaded in accordance with a scale of vasodilatation or vasoconstriction.

7. A system according to claim 1, wherein said polarizing filter provides a polarization direction orthogonal to that of polarized light from the light source and filter.

8. A system according to claim 1, wherein said polarizing filter provides a polarization direction parallel to that of polarized light from the light source and filter.

9. A system according to claim 1, comprising a reference area for producing a measurement value for normalization of the values of the said data matrixes.

10. A system according to claim 1, wherein said algorithm for generating the output data matrix employs the difference of the values of the data matrixes representing red and green colors divided by the sum of the corresponding values of the data matrixes representing red and green colors.

11. A system according to claim 1, wherein said computing device comprises an algorithm for generating compensation for tissue color using the values in the data matrixes.

12. A system according to claim 1, comprising flexible optical fibers capable of directing polarized light from the light source and filter to a body cavity and to direct backscattered light to the photosensitive array.

13. A system according to claim 1 adapted to cooperate with a mobile communication terminal capable of transmitting the output data matrix over a telecommunication network.

14. A system according to claim 13 integrated with a mobile communication terminal.

15. A system according to claim 13 having a separate mobile communication terminal connected to said system with communication links.

16. A method of determining if a patient suffers from abnormalities in microcirculation, employing the system of claim 1, comprising: (i) illuminating a tissue surface with polarized light from the light source and filter; (ii) collecting backscattered light subjected to multiple scattering events in the tissue through the polarizing filter; (iii) detecting the backscattered and polarized light by the photosensitive array and converting the detected light to a collected information of digital values; (iv) transferring the collected information in digital form to the computing device; (v) separating the collected information into data matrixes representing red, blue and green colors, respectively; (vi) generating an output data matrix by processing corresponding values in the data matrixes by an algorithm, wherein each value in said output data matrix represents the amount of influence on the microcirculation in a source of point of the tissue, thereby obtaining a representation of the red blood cell concentration of the tissue microcirculation; and (vii) comparing the output matrix data or its representation with a reference obtained from a healthy individual, or from the same patient prior to the administration of a vasoactive composition.

17. A method according to claim 16, wherein said abnormalities are representations of blood pressure drop, vascular shock or the presence of vascularized tumors.

18. A method according to claim 16, wherein said abnormalities represent complications of impaired microcirculation arriving from diabetes or Alzheimer's disease, comprising a first step of subjecting the patient to local administration of a vasoactive composition.

19. A method according to claim 18, wherein the vasoactive composition comprises at least one vasodilatating agent.

20. A method according to claim 18, wherein the vasoactive composition comprises a first agent exerting its vasodilatating activity by the smooth muscles and a second agent that exerts its vasodilatation activity by the endothelium.

21. A method according to claim 18, wherein the vasodilatating agents are selected from the group consisting of acetylcholine and sodium nitroprusside.

22. A method according to claim 18, wherein the local administration of vasoactive composition is supported with iontophoresis.

23. A system according to claim 1, wherein said algorithm for generating the output data matrix employs the difference of the values of the data matrixes representing red and green colors divided by corresponding values of the data matrix representing blue color.

24. A system according to claim 1, wherein said algorithm for generating the output data matrix employs the difference of the values of the data matrixes representing red and green colors divided by corresponding values of data matrixes representing the difference between red and blue colors.

25. A system according to claim 1, wherein said algorithm for generating the output data matrix employs the difference of the values of the data matrixes representing red and blue colors divided by corresponding values of the data matrix representing green color.

* * * * *